United States Patent [19]
Fink

[11] Patent Number: 6,034,136
[45] Date of Patent: Mar. 7, 2000

[54] CERTAIN CYCLIC THIO SUBSTITUTED ACYLAMINOACID AMIDE DERIVATIVES

[75] Inventor: Cynthia A. Fink, Lebanon, N.J.

[73] Assignee: Novartis AG, Basel, Switzerland

[21] Appl. No.: 09/040,093

[22] Filed: Mar. 17, 1998

Related U.S. Application Data

[60] Provisional application No. 60/039,845, Mar. 20, 1997.

[51] Int. Cl.$^7$ ..................... A61K 31/165; C07C 233/58; C07C 233/05
[52] U.S. Cl. .................. 514/618; 514/237.5; 514/237.8; 514/329; 514/330; 514/357; 514/423; 544/162; 544/165; 546/225; 546/329; 548/530; 548/537; 564/154; 564/153
[58] Field of Search ..................................... 564/154, 153; 514/616, 237.5, 237.8, 329, 330, 357, 423; 546/225, 329; 548/530, 537; 544/162, 165

[56] References Cited

U.S. PATENT DOCUMENTS

| | | | |
|---|---|---|---|
| 4,595,700 | 6/1986 | Donald et al. | 514/616 |
| 5,407,960 | 4/1995 | Neustadt | 514/613 |
| 5,506,244 | 4/1996 | Fink | 514/354 |

FOREIGN PATENT DOCUMENTS

| | | |
|---|---|---|
| 322184 | 6/1989 | European Pat. Off. . |
| 5-92948 | 4/1993 | Japan . |
| WO 91/09840 | 7/1991 | WIPO . |
| WO 95/12603 | 5/1995 | WIPO . |
| WO 95/13289 | 5/1995 | WIPO . |
| WO 96/11209 | 4/1996 | WIPO . |
| WO 96/40738 | 12/1996 | WIPO . |

OTHER PUBLICATIONS

Chemical Abstract 119:160823 of JP 05092948A., 1993.
Derwent Abstract of JP 05092948A., 1993.
Abstract XP–002073604 of JP 05092948A., 1993.
Annual Reports in Medicinal Chemistry, pp. 231–240 (1996).
Biorganic Med. Chem. Letters 7 (7), pp. 897–902 (1997).
J. Med. Chem. 38, 5023–5030 (1995).
Annual Reports in Medicinal Chemistry, pp. 177–184 (1989).
Biorganic Med.Chem.Letters, vol. 3, (5), pp. 825–830 (1992).
Current Drugs Abstract of WO 97/03783 A1 published on Feb. 6, 1997.
Current Drugs Abstract of WO 96/40738 published Dec. 19, 1996.
Current Drugs Abstract of WO 96/11209 published Apr. 18, 1996.

Primary Examiner—Shailendra Kumar
Attorney, Agent, or Firm—Norbert Gruenfeld

[57] ABSTRACT

Disclosed are compound of formula I

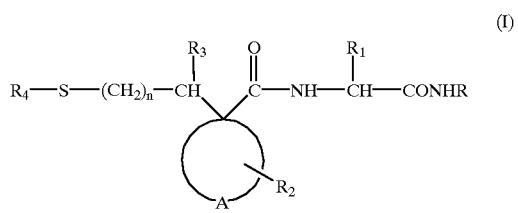

(I)

wherein

R represents hydrogen, lower alkyl, cycloalkyl, bicycloalkyl, adamantyl, aryl, biaryl, or mono- or di-(cycloalkyl, aryl or biaryl)-lower alkyl, di-(lower alkyl or aryl-lower alkyl)amino-lower alkyl, or (piperidino, morpholino, pyrrolidino)-lower alkyl;

$R_1$ represents hydrogen, lower alkyl, cycloalkyl, aryl, biaryl, or (cycloalkyl, aryl or biaryl)-lower alkyl;

$R_2$ represents hydrogen, lower alkyl, lower alkoxy, aryl-lower alkyl, aryl-lower alkoxy, amino, mono- or di-(lower alkyl or aryl-lower alkyl)-amino, acylamino, or (lower alkyl or aryl-lower alkyl)-(thio, sulfinyl or sulfonyl);

$R_3$ represents hydrogen, lower alkyl, cycloalkyl, aryl-lower alkyl, cycloalkyl-lower alkyl, or $C_2$–$C_7$-alkyl interrupted by S, SO, $SO_2$, O or N—$R_5$;

$R_4$ represents hydrogen or acyl;

$R_5$ represents hydrogen, lower alkyl, aryl-lower alkyl, acyl, or (lower alkyl, aryl or aryl-lower alkyl)-sulfonyl;

A together with the carbon to which it is attached forms a ring and represents a bivalent radical of the formula $(CH_2)_p$ which may be interrupted by S, SO, $SO_2$, O, or N—$R_5$;

n represents an integer from zero to four;

p represents an integer from 2 to 6;

any pharmaceutically acceptable salts thereof;

and disulfides corresponding to said compounds of formula I wherein $R_4$ is hydrogen;

methods for preparation thereof;

pharmaceutical compositions comprising said compounds;

and a method of inhibiting matrix-degrading metalloproteinases in mammals using such compounds.

19 Claims, No Drawings

CERTAIN CYCLIC THIO SUBSTITUTED ACYLAMINOACID AMIDE DERIVATIVES

CROSS-REFERENCE TO RELATED APPLICATIONS

This application claims the benefit of provisional application No. 60/039,845, filed Mar. 20, 1997.

SUMMARY OF THE INVENTION

The present invention relates to novel thio substituted cyclic acylaminoacid amide derivatives described below, as inhibitors of matrix-degrading metalloproteinases and TNF alpha (tissue necrosis factor alpha) activity, methods for preparation thereof, pharmaceutical compositions comprising said compounds, a method of inhibiting TNF alpha and matrix degrading metalloproteinase activity and a method of treating TNF alpha and matrix metalloproteinase dependent diseases or conditions in mammals which are responsive to matrix metalloprotease and TNF alpha inhibition, using such compounds or pharmaceutical compositions comprising such compounds of the invention.

The compounds of the invention inhibit matrix degrading metalloproteinases such as gelatinase, stromelysin, collagenase, macrophage metalloelastase, and also membrane-type matrix metallo-proteinases such as MT-MMP 1 and 2. They are particularly useful as collagenase-3 inhibitors. Compounds of the invention are also inhibitors of TNF-alpha converting enzyme (TNF-alpha convertase) and thus inhibit TNF alpha activity, e.g. suppress the production and/or release of TNF alpha, an important mediator of inflammation and tissue growth.

Thus the compounds of the invention inhibit matrix degradation and are useful for the treatment of gelatinase-, stromelysin-, collagenase-, TNF alpha-, MT-MMP-1 and 2-, and macrophage metalloelastase-dependent pathological conditions in mammals. Such conditions include malignant and non-malignant tumors (by inhibiting tumor growth, tumor metastasis, tumor progression or invasion and/or tumor angiogenesis), such tumors including e.g. breast, lung, bladder, colon, ovarian and skin cancer. Other conditions to be treated with the compounds of the invention include rheumatoid arthritis, osteoarthritis, bronchial disorders (such as asthma by inhibiting the degradation of elastin), atherosclerotic conditions (by e.g. inhibiting rupture of atherosclerotic plaques), as well as acute coronary syndrome, heart attacks (cardiac ischemia), strokes (cerebral ischemias), restenosis after angioplasty, and also vascular ulcerations, ectasia and aneurysms.

Further conditions to be treated with the compounds of the invention are inflammatory demyelinating disorders of the nervous system in which myelin destruction or loss is involved (such as multiple sclerosis), optic neuritis, neuromyelitis optica (Devic's disease), diffuse and transitional sclerosis (Schilder's disease) and acute disseminated encephalomyelitis, also demyelinating peripheral neuropathies, such as Landry-Guillain-Barre-Strohl syndrome for motor defects; also tissue ulceration (e.g. epidermal and gastric ulceration), abnormal wound healing, periodental disease, bone disease (e.g. Paget's disease and osteoporosis), also endometriosis, septic shock, inflammatory bowel disease, Crohn's disease and the like.

Ocular applications of the compounds of the invention include the treatment of ocular inflammation, corneal ulcerations, pterygium, keratitis, keratoconus, open angle glaucoma, retinopathies, and also their use in conjunction with refractive surgery (laser or incisional) to minimize adverse effects.

DETAILED DESCRIPTION OF THE INVENTION

The present invention relates to the cyclic thio substituted acylaminoacid amide derivatives of formula I

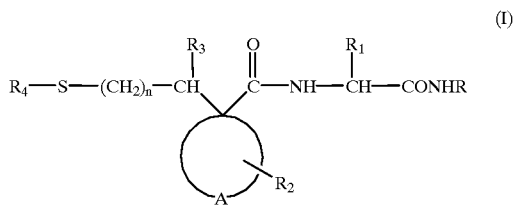

wherein

R represents hydrogen, lower alkyl, cycloalkyl, bicycloalkyl, adamantyl, aryl, biaryl, or mono- or di-(cycloalkyl, aryl or biaryl)-lower alkyl, di-(lower alkyl or aryl-lower alkyl)-amino-lower alkyl, or (piperidino, morpholino, pyrrolidino)-lower alkyl;

$R_1$ represents hydrogen, lower alkyl, cycloalkyl, aryl, biaryl, or (cycloalkyl, aryl or biaryl)-lower alkyl;

$R_2$ represents hydrogen, lower alkyl, lower alkoxy, aryl-lower alkyl, aryl-lower alkoxy, amino, mono- or di-(lower alkyl or aryl-lower alkyl)-amino, acylamino, or (lower alkyl or aryl-lower alkyl)-(thio, sulfinyl or sulfonyl);

$R_3$ represents hydrogen, lower alkyl, cycloalkyl, aryl-lower alkyl, cycloalkyl-lower alkyl, or $C_2$–$C_7$-alkyl interrupted by S, SO, $SO_2$, O or N—$R_5$;

$R_4$ represents hydrogen or acyl;

$R_5$ represents hydrogen, lower alkyl, aryl-lower alkyl, acyl, or (lower alkyl, aryl or aryl-lower alkyl)-sulfonyl;

A together with the carbon to which it is attached forms a ring and represents a bivalent radical of the formula $(CH_2)_p$ which may be interrupted by S, SO, $SO_2$, O, or N—$R_5$;

n represents zero or an integer from one to four;

p represents an integer from 2 to 6;

any pharmaceutically acceptable salts thereof; and disulfides corresponding to said compounds of formula I wherein $R_4$ is hydrogen.

The compounds of the invention depending on the nature of the substituents, possess one or more asymmetric carbon atoms. Also the A-containing ring substituent $R_2$ is either cis or trans to the amide grouping. The resulting diastereoisomers, enantiomers and geometric isomers are encompassed by the instant invention.

Preferred are the compounds of the invention wherein the configuration of the asymmetric carbon atom of the terminal amino acid amide moiety corresponds to that of an L-amino acid precursor and is assigned the (S)-configuration.

Further preferred are the compounds of formula I in which the A-containing ring is e.g. cyclohexane in which the substituent $R_2$ is at the 4-position and is preferably cis to the amide grouping.

Compounds in which $R_4$ is acyl represent prodrug acyl derivatives and are preferably those derived from an organic carbonic acid, an organic carboxylic acid or a carbamic acid.

An acyl derivative which is derived from an organic carboxylic acid is, for example, lower alkanoyl, phenyl-lower alkanoyl or unsubstituted or substituted aroyl, such as benzoyl.

An acyl derivative which is derived from an organic carbonic acid is, for example, alkoxycarbonyl, especially lower alkoxycarbonyl, which is unsubstituted or substituted by carbocyclic or heterocyclic aryl or is cycloalkoxycarbonyl, especially $C_3$–$C_7$-cycloalkyloxycarbonyl, which is unsubstituted or substituted by lower alkyl.

An acyl derivative which is derived from a carbamic acid is, for example, aminocarbonyl which is substituted by lower alkyl, carbocyclic or heterocyclic aryl-lower alkyl, carbocyclic or heterocyclic aryl, lower alkylene or lower alkylene interrupted by O or S.

Pharmaceutically acceptable salts of any acidic compounds of the invention are salts formed with bases, namely cationic salts such as alkali and alkaline earth metal salts, such as sodium, lithium, potassium, calcium, magnesium, as well as ammonium salts, such as ammonium, trimethylammonium, diethylammonium, and tris-(hydroxymethyl)-methylammonium salts.

Similarly acid addition salts, such as of mineral acids, organic carboxylic, and organic sulfonic acids e.g. hydrochloric acid, methanesulfonic acid, maleic acid, are possible provided a basic group, such as pyridyl, constitutes part of the structure.

The general definitions used herein have the following meaning within the scope of the present invention, unless otherwise specified.

The term "lower" referred to above and hereinafter in connection with organic radicals or compounds respectively defines such as branched or unbranched with up to and including 7, preferably up to and including 4 and advantageously one or two carbon atoms.

A lower alkyl group is branched or unbranched and contains 1 to 7 carbon atoms, preferably 1–4 carbon atoms, and represents for example methyl, ethyl, propyl, butyl, isopropyl or isobutyl. Lower alkyl for $R_1$ is preferably $C_2$–$C_5$-alkyl, advantageously $C_2$–$C_4$-alkyl.

Lower alkylene in general represents either straight chain or branched alkylene of 1 to 7 carbon atoms and represents preferably straight chain alkylene of 1 to 4 carbon atoms, e.g. a methylene, ethylene, propylene or butylene chain , or said methylene, ethylene, propylene or butylene chain mono-substituted by $C_{1-3}$-alkyl (advantageously methyl) or disubstituted on the same or different carbon atoms by $C_1$–$C_3$-alkyl (advantageously methyl), the total number of carbon atoms being up to and including 7.

Lower alkylenedioxy is preferably ethylenedioxy or methylenedioxy.

Esterified carboxyl is for example lower alkoxycarbonyl or benzyloxycarbonyl.

Amidated carboxyl is for example aminocarbonyl, mono- or di-lower alkylaminocarbonyl.

Alkylene interrupted by O, S, SO, $SO_2$ or N—$R_5$ (representing bivalent radical A) preferably represents butylene or pentylene interrupted by O, S, SO, $SO_2$ or N—$R_5$.

A lower alkoxy (or alkyloxy) group preferably contains 1–4 carbon atoms, and represents for example methoxy, ethoxy, propoxy, isopropoxy, butoxy or isobutoxy.

Halogen (or halo) preferably represents chloro or fluoro but may also be bromo or iodo.

Aryl represents carbocyclic or heterocyclic aryl.

Carbocyclic aryl represents monocyclic or bicyclic aryl, for example phenyl or phenyl mono-, di- or tri-substituted by one, two or three radicals selected from lower alkyl, lower alkoxy, hydroxy, halogen, cyano, carboxyl, esterified carboxyl, amidated carboxyl, trifluoromethyl, amino, mono- or dialkylamino, trifluoromethoxymethyl, lower alkyl-thio, sulfinyl or sulfonyl, lower alkylenedioxy and oxy-$C_2$–$C_3$-alkylene; or 1- or 2-naphthyl. Lower alkylenedioxy is a divalent substituent attached to two adjacent carbon atoms of phenyl, e.g. methylenedioxy or ethylenedioxy. Oxy-$C_2$–$C_3$-alkylene is also a divalent substituent attached to two adjacent carbon atoms of phenyl, e.g. oxyethylene or oxypropylene. An example for oxy-$C_2$–$C_3$-alkylene-phenyl is 2,3-dihydrobenzofuran-5-yl.

Preferred as carbocyclic aryl is phenyl or phenyl monosubstituted by lower alkoxy, halogen, lower alkyl or trifluoromethyl, especially phenyl or phenyl monosubstituted by lower alkoxy, halogen or trifluoromethyl, and in particular phenyl.

Heterocyclic aryl represents monocyclic or bicyclic heteroaryl, for example pyridyl, quinolinyl, isoquinolinyl, benzothienyl, benzofuranyl, benzopyranyl, benzothiopyranyl, furanyl, pyrrolyl, thiazolyl, oxazolyl, isoxazolyl, triazolyl, tetrazolyl, pyrazolyl, imidazolyl, thienyl, or any said radical substituted, especially mono- or di-substituted, by e.g. lower alkyl or halogen. Pyridyl represents 2-, 3- or 4-pyridyl, advantageously 3- or 4-pyridyl. Thienyl represents 2- or 3-thienyl, advantageously 3-thienyl. Quinolinyl represents preferably 2-, 3- or 4-quinolinyl, advantageously 2-quinolinyl. Isoquinolinyl represents preferably 1-, 3- or 4-isoquinolinyl. Benzopyranyl, benzothiopyranyl represent preferably 3-benzopyranyl or 3-benzothiopyranyl, respectively. Thiazolyl represents preferably 2- or 4-thiazolyl, advantageously 4-thiazolyl. Triazolyl is preferably 1-, 2- or 5-(1,2,4-triazolyl). Tetrazolyl is preferably 5-tetrazolyl. Imidazolyl is preferably 4-imidazolyl.

Preferably, heterocyclic aryl is pyridyl, quinolinyl, pyrrolyl, thiazolyl, isoxazolyl, triazolyl, tetrazolyl, pyrazolyl, imidazolyl, thienyl, or any said radical substituted, especially mono- or di-substituted, by lower alkyl or halogen; and in particular pyridyl.

Biaryl is preferably carbocyclic biaryl, e.g. biphenyl, namely 2-, 3- or 4-biphenyl, advantageously 4-biphenyl, each optionally substituted by e.g. lower alkyl, lower alkoxy, halogen, trifluoromethyl or cyano.

Cycloalkyl represents a saturated cyclic hydrocarbon optionally substituted by lower alkyl which contains 3 to 10 ring carbons and is advantageously cyclopentyl, cyclohexyl, cycloheptyl or cyclooctyl optionally substituted by lower alkyl.

Bicycloalkyl represents bornyl, norbornyl and the like.

Carbocyclic aryl-lower alkyl represents preferably straight chain or branched aryl-$C_1$–$C_4$-alkyl in which carbocyclic aryl has meaning as defined above, e.g. benzyl or phenyl-(ethyl, propyl or butyl), each unsubstituted or substituted on phenyl ring as defined under carbocyclic aryl above, advantageously optionally substituted benzyl.

Heterocyclic aryl-lower alkyl represents preferably straight chain or branched heterocyclic aryl-$C_{1-4}$-alkyl in which heterocyclic aryl has meaning as defined above, e.g. 2-, 3- or 4-pyridylmethyl or (2-, 3- or 4-pyridyl)-(ethyl, propyl or butyl); or 2- or 3-thienylmethyl or (2- or 3-thienyl)-(ethyl, propyl or butyl); 2-, 3- or 4quinolinylmethyl or (2-, 3- or 4quinolinyl)-(ethyl, propyl or butyl); or 2- or 4-thiazolylmethyl or (2- or 4-thiazolyl)-(ethyl, propyl or butyl).

Cycloalkyl-lower alkyl represents e.g. (cyclopentyl- or cyclohexyl)-(methyl or ethyl).

Acyl is derived from an organic carboxylic acid, carbonic acid or carbamic acid.

Acyl represents e.g. lower alkanoyl, carbocyclic aryl-lower alkanoyl, lower alkoxycarbonyl, aroyl, di-lower alkylaminocarbonyl, di-lower alkylamino-lower alkanoyl (piperidine, morpholine or pyrrolidine)-cabonyl, (piperidino, morpholino or pyrrolidino)-lower alkanoyl or lower alkoxy-lower alkanoyl. Preferably, acyl is lower alkanoyl.

Lower alkanoyl represents e.g. $C_1$–$C_7$-alkanoyl including formyl, and is preferably $C_2$–$C_4$-alkanoyl such as acetyl or propionyl.

Aroyl represents e.g. benzoyl or benzoyl mono- or di-substituted by one or two radicals selected from lower alkyl, lower alkoxy, halogen, cyano and trifluoromethyl; or 1- or 2-naphthoyl; and also heterocyclic aroyl, e.g. pyridyl-carbonyl.

Lower alkoxycarbonyl represents preferably $C_1$–$_4$-alkoxycarbonyl, e.g. ethoxycarbonyl.

Preferred embodiments of the invention relate to the compounds of formula I wherein the A-containing ring is a cyclopropane, cyclopentane, cyclohexane, tetrahydropyran, tetrahydrofuran, pyrrolidine or piperidine ring.

A particular embodiment of the invention relates to the compounds of formula II

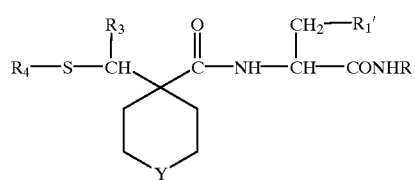

(II)

wherein

R, $R_3$, $R_4$ and $R_5$ have meaning as defined above, $R_1'$ represents cycloalkyl, aryl or biaryl; and Y represents $CHR_2$, S, SO, $SO_2$, O, or $NR_5$.

A further embodiment relates to the compounds of formula III

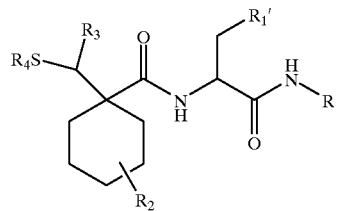

(III)

wherein R is carbocyclic or heterocyclic aryl, carbocyclic or heterocyclic aryl-lower alkyl, cycloalkyl or lower alkyl; $R_1'$ is carbocyclic or heterocyclic aryl, or biaryl; $R_2$ is hydrogen, lower alkyl or lower alkoxy; $R_3$ is hydrogen, lower alkyl or carbocyclic aryl-lower alkyl; and $R_4$ is hydrogen, lower alkanoyl, aryl-lower alkanoyl or aroyl.

Preferred are said compound of formula III wherein $R_2$ is at the 4-position of the cyclohexane ring.

Further preferred are compounds of formula IV

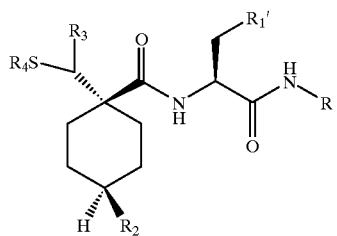

(IV)

wherein, $R_2$ and the amide chain are cis to each other, and R, $R_1'$, $R_2$ and $R_4$ have meaning as defined hereinabove.

Preferred in turn are said compounds of formula IV wherein R is monocyclic carbocyclic or heterocyclic aryl; $R_1'$ is monocyclic carbocyclic aryl; $R_2$ is lower alkoxy; $R_3$ is hydrogen; and $R_4$ is hydrogen or lower alkanoyl.

The compounds of the invention exhibit valuable pharmacological properties in mammals including man.

The compounds of the invention inhibit matrix degrading metalloproteinase such as gelatinase, stromelysin, collagenase, (including collagenase 1 and 3), and macrophage metalloelastase, and membrane type matrix metalloproteinases, such as MT-MMP 1 and 2. They are particularly useful as collagenase-3 inhibitors. Compounds of the invention are also inhibitors of TNF-alpha converting enzyme (TNF-alpha convertase) and thus inhibit TNF alpha activity, e.g. suppress the production and/or release of TNF alpha, an important mediator of inflammation and tissue growth.

Thus the compounds of the invention inhibit matrix degradation and are useful for the treatment of gelatinase-, stromelysin-, collagenase-, TNF alpha- and macrophage metalloelastase-dependent pathological conditions in mammals. Such conditions include malignant and non-malignant tumors (by inhibiting tumor growth, tumor metastasis, tumor progression or invasion and/or tumor angiogenesis), such tumors including e.g. breast, lung, bladder, colon, ovarian, and skin cancer. Other conditions to be treated with the compounds of the invention include rheumatoid arthritis osteoarthritis, bronchial disorders (such as asthma by inhibiting the degradation of elastin), atherosclerotic conditions (by e.g. inhibiting rupture of atherosclerotic plaques), as well as acute coronary syndrome, heart attacks (cardiac ischemia), strokes (cerebral ischemias), restenosis after angioplasty, and also vascular ulcerations, ectasia and aneurysms.

Further conditions to be treated with the compounds of the invention are inflammatory demyelinating disorders of the nervous system in which myelin destruction or loss is involved (such as multiple sclerosis), optic neuritis, neuromyelitis optica (Devic's disease), diffuse and transitional sclerosis (Schilder's disease) and acute disseminated encephalomyelitis, also demyelinating peripheral neuropathies such as Landry-Guillain-Barre-Strohl syndrome for motor defects; also tissue ulceration (e.g. epidermal and gastric ulceration), abnormal wound healing, periodental disease, bone disease (e.g. Paget's disease and osteoporosis). Also endometriosis, septic shock, inflammatory bowel disease, Crohn's disease and the like.

Ocular applications of the compounds of the invention include the treatment of ocular inflammation, corneal ulcerations, pterygium, keratitis, keratoconus, open angle glaucoma, retinopathies, and also their use in conjunction with refractive surgery (laser or incisional) to minimize adverse effects.

The compounds are particularly useful for the treatment of e.g. inflammatory conditions, osteoarthritis, rheumatoid arthritis and tumors.

Beneficial effects are evaluated in pharmacological tests generally known in the art, and as illustrated herein.

The above-cited properties are demonstrable in in vitro and in vivo tests, using advantageously mammals, e.g. rats, guinea pigs, dogs, rabbits, or isolated organs and tissues, as well as mammalian enzyme preparations. Said compounds can be applied in vitro in the form of solutions, e.g. preferably aqueous solutions, and in vivo either enterally or parenterally, advantageously orally, e.g. as a suspension or in aqueous solution. The dosage in vitro may range between about $10^{-5}$ molar and $10^{-10}$ molar concentrations. The dosage in vivo may range, depending on the route of administration, between about 0.1 and 100 mg/kg.

The inhibition of the production and secretion of TNF-alpha (by inhibition of TNF-αconvertase) can be determined e.g. as described in Nature 370, 555, 558 (1994).

The effect on the production of soluble TNF-alpha by LPS-stimulated THP-1 cells can be determined as follows:

Tissue culture medium used is RPM 1640 (Gibco cat #11875-036) containing 10% fetal calf serum, 1% penicillin and streptomycin. THP-1 cells (ATCC #202-TIB) at $1\times10^{+5}$ cells/well are added to 100 μl medium or test compound. Cells are pre-incubated with compound for 30 minutes in a 37° C. humidified chamber with 5% $CO_2$ and then stimulated with 100 ng/ml of LPS (Sigma cat #L-4391) for 4 hours. Plates are then centrigued and 100 μl of conditioned medium for TNF analysis is harvested. The amount of TNF-alpha in control and test cultures is determined by ELISA using recombinant TNF-alpha for the standard curve, using TNF ELISA plates (Genzyme) for TNF analysis. Absorbance readings and data calculations are performed on a Molecular Devices plate reader. Results are expressed in $IC_{50}$'s of test compound.

The effect on the plasma concentration of TNF-alpha in the mouse following intravenous injection of endotoxin can be determined as follows:

Female Balb-CbyJ mice are dosed by gavage with test compound in 0.1 mL cornstarch vehicle/10 grams body weight. One to four hours after administration of test compound, 0.1 mg/kg Lipopolysaccharide from E. coli 0127:B8 (Difco #3880-25-0) in saline is injected i.v. One hour after i.v. injection of LPS, blood is collected for determination of plasma TNF-alpha using mouse TNF-alpha ELISA kit (Genzyme). Eight mice are used per treatment group. Results are expressed as % inhibition of mean TNF-alpha concentration in control mice.

The effect on the synovial fluid concentration of TNF-alpha in an inflamed rat knee can be determined as follows:

Female Lewis rats are dosed by gavage with test compound in 0.1 mL cornstarch vehicle. One to four hours after administration of test compound 0.1 mg Lipopolysaccharide from E. coli 0127:B8 (Difco #3880-25-0) is injected into both knees. Two hours after intra-articular LPS injection, knees are lavaged with 0.1 ml saline and 2 lavages from same rat are pooled. TNF-alpha is measured using mouse TNF-alpha ELISA kit (Genzyme) which crossreacts with rat TNF-alpha. Results are expressed as % inhibition of mean TNF-alpha concentration in synovial fluid from saline-injected knees.

Antiinflammatory activity can be determined in standard inflammation and arthritic animal models well-known in the art, e.g. the adjuvant arthritis model in rats and the collagen II induced arthritis model in mice (Mediators of Inflam. 1, 273–279 (1992).

One test to determine the inhibition of stromelysin activity is based on its hydrolysis of Substance P using a modified procedure of Harrison et al (Harrison, R. A., Teahan J., and Stein R., A semicontinuous, high performance chromatography based assay for stromelysin, Anal. Biochem. 180, 110–113 (1989)). In this assay, Substance P is hydrolyzed by recombinant human stromelysin to generate a fragment, Substance P 7-11, which can be quantitated by HPLC. In a typical assay, a 10 mM stock solution of a compound to be tested is diluted in the assay buffer to 50 μM, mixed 1:1 with 8 μg recombinant human stromelysin (mol. wt. 45–47 kDa, 2 Units; where 1 Unit produces 20 mmoles of Substance P 7-11 in 30 minutes) and incubated along with 0.5 mM Substance P in a final volume of 0.125 ml for 30 minutes at 37° C. The reaction is stopped by adding 10 mM EDTA and Substance P 7-11 is quantified on RP-8 HPLC. The IC50 for inhibition of stromelysin activity and Ki are calculated from control reaction without the inhibitor.

Compounds of formula I have an $IC_{50}$ of about 10 nM to about 5 μM for inhibition of stromelysin activity. Illustrative of the invention the compound of example 2(e) exhibits an IC50 of about 70 nM in this assay.

Stromelysin activity can also be determined using human aggrecan as a substrate. This assay allows the confirmation in-vitro that a compound can inhibit the action of stromelysin on its highly negatively-charged natural substrate, aggrecan (large aggregating prtoeoglycan). Within the cartilage, proteoglycan exists as an aggregate bound to hyaluronate. Human proteoglycan aggregated to hyaluronate is used as an enzyme substrate. The assay is set up in 96-well microtiter plates allowing rapid evaluation of compounds. The assay has three major steps:

1) Plates are coated with hyaluronate (human umbilical chord, 400 ug/ml), blocked with BSA (5 mg/ml), and then proteoglycan (human articular cartilage D1—chondroitinase ABC digested, 2 mg/ml) is bound to the hyaluronate. Plates are washed between each step.

2) Buffers+inhibitor (1 to 5,000 nM)+recombinant human stromelysin (1–3 Units/well) are added to wells. The plates are sealed with tape and incubated overnight at 37° C. The plates are then washed.

3) A primary (3B3) antibody (mouse IgM, 1:10,000) is used to detect remaining fragments. A secondary antibody, peroxididase-linked anti-IgM, is bound to the primary antibody. OPD is then added as a substrate for the peroxidase and the reaction is stopped with sulfuric acid. The $IC_{50}$ for inhibition of stromelysin activity is graphically derived and Ki is calculated.

Collagenase −1 inhibitory activity is determined as follows: ninety six-well, flat-bottom microtiter plates are first coated with bovine type I collagen (35 ug/well) over a two-day period at 30° C. using a humidified and then dry atmosphere; plates are rinsed, air dried for 3–4 hours, sealed with Saran wrap and stored in a refrigerator. Human recombinant fibroblast collagenase and a test compound (or buffer) are added to wells (total volume=0.1 ml) and plates are incubated for 2 hours at 35° C. under humidified conditions; the amount of collagenase used per well is that causing approximately 80% of maximal digestion of collagen. The incubation media are removed from the wells, which are then rinsed with buffer, followed by water. Coomasie blue stain is added to the wells for 25 minutes, removed, and wells are again rinsed with water. Sodium dodecyl sulfate (20% in 50% dimethylformamide in water) is added to solubilize the remaining stained collagen and the optical density at 570 nM wave length is measured. The decrease in optical density due to collagenase (from that of collagen without enzyme) is compared to the decrease in optical density due to the enzyme in the presence of test compound, and percent inhibition of enzyme activity is calculated. $IC_{50}$'s are determined from a range of concentrations of inhibitors (4–5 concentrations, each tested in triplicate), and $K_I$ values are calculated.

Compounds of formula I have an $IC_{50}$ of about 5 μM to about 5 μM for inhibition of collagenase-1 activity. Illustrative of the invention, the compound of example 2(d) exhibits an $IC_{50}$ of about 200 nM.

Collagenase-3 inhibitory activity is determined as follows:

One nM stock solutions of substrate (MCA-Pro-Leu-Gly-Dpa-Ala-Arg-$NH_2$, J. Biol. Chem. 271, 1544–1550, 1996) and 10 nM stock solution of inhibitor are prepared in DMSO. They are diluted with assay buffer (20 nM tris at pH 7.5 containing 10 mM $CaCl_2$, 0.002% sodium azide) as needed. Recombinant pro-collagenase-3 is activated with 1 mM APMA, and stored in the assay buffer after extensive dialysis in the assay buffer. Recombinant enzyme solution (0.05 ml, 1.3 nM) is mixed with 0.05 mL of inhibitor solution at various concentrations for 10 minutes at room temperature. Then 0.025 mL of 8 μM substrate solution is added and fluorescence (λex=325; λem=405) is continuously measured at room temperature. The percent inhibition of collagenase-3 activity is determined from the effect of inhibitor at various concentrations on the change in fluorescence; the $IC_{50}$ is determined graphically.

Compounds of formula I have an $IC_{50}$ of about 5 nM to about 100 nM for inhibition of collagenase-3 activity. Illustrative of the invention, the compound of example 2(d) exhibits an $IC_{50}$ of about 20 nM.

The effect of compounds of the invention in-vivo can be determined in rabbits. Typically, four rabbits are dosed orally with a compound up to four hours before being injected intra-articularly in both knees (N=8) with 40 Units of recombinant human stromelysin dissolved in 20 mM Tris, 10 mM $CaCl_2$, and 0.15 M NaCl at pH 7.5. Two hours later the rabbits are sacrificed, synovial lavage is collected, and keratan sulfate (KS) and sulfated glycosaminoglycan (S-GAG) fragments released into the joint are quantitated. Keratan sulfate is measured by an inhibition ELISA using the method of Thonar (Thonar, E. J.-M. A., Lenz, M. E., Klinsworth, G. K., Caterson, B., Pachman, L. M., Glickman, P., Katz, R., Huff, J., Keuttner, K. E. Quantitation of keratan sulfate in blood as a marker of cartilage catabolism, Arthr. Rheum. 28, 1367–1376 (1985)). Sulfated glycosaminoglycans are measured by first digesting the synovial lavage with streptomyces hyaluronidase and then measuring DMB dye binding using the method of Goldberg (Goldberg, R. L. and Kolibas, L. An improved method for determining proteoglycan synthesized by chondrocytes in culture. Connect. Tiss. Res. 24, 265–275 (1990)). For an i.v. study, a compound is solubilized in 1 mL of PEG400, and for a p.o. study, a compound is administered in 5 ml of fortified corn starch per kilogram of body weight.

The effect in protecting against cartilage degradation in arthritic disorders can be determined e.g. in a surgical model of osteoarthritis described in Arthritis and Rheumatism, Vol. 26, 875–886 (1983).

The effect on ulcerations, e.g. ocular ulcerations, can be determined in the rabbit by measuring the reduction of corneal ulceration following an alkali bum to the cornea.

Macrophage metalloelastase (MME) inhibitory activity can be determined by measuring the inhibition of the degradation of [$^3$H]-elastin by truncated recombinant mouse macrophage metalloelastase as follows:

About 2 ng of recombinant truncated mouse macrophage metalloelastase (FASEB Journal Vol. 8, A151, 1994), purified by Q-Sepharose column chromatography is incubated with test compounds at the desired concentrations in the presence of 5 nM $CaCl_2$, 400 nM NaCl, [$^3$H]elastin (60,000 cpm/tube), and 20 mM Tris, pH 8.0, at 37° C. overnight. The samples are spun in a microfuge centrifuge at 12,000 rpm for 15 minutes. An aliquot of the supernatant is counted in a scintillation counter to quantitate degraded [$^3$H]elastin. $IC_{50}$'s are determined from a range of concentrations of the test compounds and the percent inhibition of enzyme activity obtained.

The effect of the compounds of the invention for the treatment of emphysema can be determined in animal models described in American Review of Respiratory Disease 117, 1109 (1978).

The antitumor effect of the compounds of the invention can be determined e.g. by measuring the growth of human tumors implanted subcutaneously in Balb/c nude treated mice according to methodology well-known in the art in comparison to placebo treated mice. Illustrative tumors are e.g. estrogen dependent human breast carcinoma BT20 and MCF7, human bladder carcinoma T24, human colon carcinoma Colo 205, human lung adenocarcinoma A549 and human ovarian carcinoma NIH-$OVCAR_3$.

The effect on tumor angiogenesis can be determined e.g. in rats implanted with Walker 256 carcinoma in pellets to stimulate angiogenesis from vessels of the limbus, as described by Galardy et al, Cancer Res. 54, 4715 (1994).

The effect of the compounds of the invention on atherosclerotic conditions can be evaluated using atherosclerotic plaques from cholesterol-fed rabbits which contain activated matrix metalloproteinases as described by Sukhova et al, Circulation 90,I 404 (1994). The inhibitory effect on matrix metalloproteinase enzyme activity in rabbit atherosclerotic plaques can be determined by in situ zymography, as described by Galis et al, J. Clin. Invest. 94, 2493 (1994), and is indicative of plaque rupture.

The effect on vascular aneurysms, e.g. the inhibition of aneurysm formation, can be determined in experimental models such as Apo-E transgenic mice and/or LDL receptor knockout mice.

The effect on restenosis and vascular remodeling can be evaluated in the rat balooned carotid artery model.

The effect on demyelinating disorders of the nervous system, such as multiple sclerosis, can be evaluated by measuring the reversal of experimental autoimmune encephalomyelitis in mice, e.g. as described by Gijbels et al, J. Clin. Invest. 94, 2177 (1994).

The compounds of the invention are particularly useful in mammals as antiinflammatory agents for the treatment of e.g. osteoarthritis, rheumatoid arthritis, and as antitumor agents for the treatment and prevention of tumors growth, tumor metastasis, tumor invasion or progression and as antiatherosclerotic agents for the treatment and prevention of the rupture of atherosclerotic plaques.

The compounds of the invention, can be prepared by condensing under basic conditions a reactive intermediate of the formula V

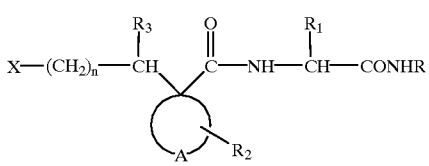

wherein R, $R_1$, $R_2$, $R_3$, n and A have meaning as previously defined, X represents a leaving group, e.g. a reactive esterified hydroxy group (such as bromo or (aryl- or alkyl)-sulfonyloxy) with a compound of the formula VI $R_4'$—SH (VI)

or a metal salt thereof, wherein $R_4'$ represents an S-protecting group, e.g. acyl, t-butyl or optionally substituted benzyl; and further converting a resulting product of formula VII

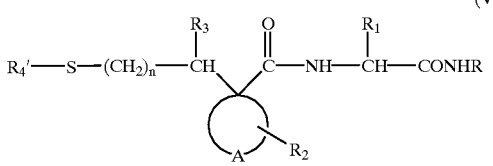

wherein $R_4'$ is t-butyl or optionally substituted benzyl to a corresponding compound of formula I wherein $R_4$ is hydrogen;
and, if necessary, temporarily protecting any interfering reactive group(s), and then liberating the resulting compound of the invention; and, if required or desired, converting a resulting compound of the invention into another compound of the invention, and/or, if desired, converting a resulting free compound into a salt or a resulting salt into a free compound or into another salt; and/or separating a mixture of isomers or racemates obtained into the single isomers or racemates; and/or, if desired, resolving a racemate into the optical antipodes.

A reactive esterified hydroxy group in a compound of formula V represents hydroxy esterified by a strong acid, especially a strong inorganic acid, such as a hydrohalic acid, especially hydrochloric, hydrobromic or hydroiodic acid, or by a strong organic acid, especially a strong organic sulfonic acid, such as an aliphatic or aromatic sulfonic acid, for example methanesulfonic acid, 4-methylbenzene sulfonic acid or 4-bromobenzenesulfonic acid. A said reactive esterified derivative is especially halogen, for example chloro, bromo or iodo, or aliphatically or aromatically substituted sulfonyloxy, for example methanesulfonyloxy, 4-methylbenzenesulfonyloxy (tosyloxy) or trifluoromethanesulfonyloxy.

The above process for the synthesis of compounds of the invention can be carried out according to reactions generally known in the art.

The reaction is carried out in an inert solvent, such as acetonitrile, dimethylformamide, or methylene chloride, in the presence of a base such as potassiuim carbonate, triethylamine, disopropylethylamine, N-methylmorpholine and the like, at room or elevated temperature, or optionally with a preformed salt of said compound of formula VI (e.g. the potassium salt).

In starting compounds and intermediates which are converted to the compounds of the invention in a manner described herein, functional groups present, such as amino, thiol, carboxyl, and hydroxy groups, are optionally protected by conventional protecting groups that are common in preparative organic chemistry. Protected amino, thiol, carboxyl, and hydroxy groups are those that can be converted under mild conditions into free amino and hydroxy groups without the molecular framework being destroyed or other undesired side reactions taking place.

The purpose of introducing protecting groups is to protect the functional groups from undesired reactions with reaction components under the conditions used for carrying out a desired chemical transformation. The need and choice of protecting groups for a particular reaction is known to those skilled in the art and depends on the nature of the functional group to be protected (hydroxy group, amino group, etc.), the structure and stability of the molecule of which the substituent is a part and the reaction conditions.

Well-known protecting groups that meet these conditions and their introduction and removal are described, for example, in J. F. W. McOmie, "Protective Groups in Organic Chemistry", Plenum Press, London, New York, 1973, T. W. Greene, "Protective Groups in Organic Synthesis", Wiley, New York, 1991.

In the processes cited herein, reactive functional derivatives of carboxylic acids represent, for example, anhydrides (especially mixed anhydrides), acid halides, acid azides, lower alkyl esters, and activated esters thereof. Mixed anhydrides are preferably such from pivalic acid, or a lower alkyl (ethyl, isobutyl) hemiester of carbonic acid; acid halides are for example chlorides or bromides; activated esters for example succinimido, phthalimido or 4-nitrophenyl esters; lower alkyl esters are for example the methyl or ethyl esters.

The starting materials of formula V can in turn be prepared from a corresponding compound of the formula VIII

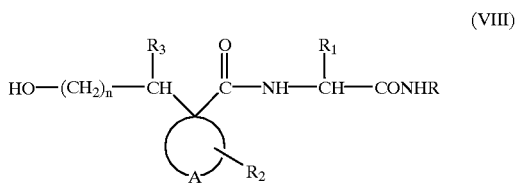

according to methods well-known in the art, e.g. by treatment with methanesulfonyl chloride in an inert solvent (such as methylene chloride) and in the presence of a base, such as triethylamine.

The intermediates of formula VIII can in turn be prepared by condensation of a compound of formula IX

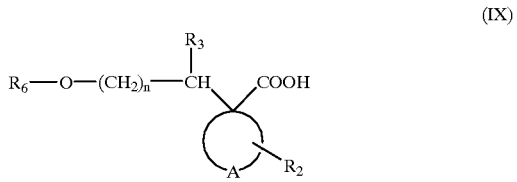

or a reactive functional derivative thereof wherein $R_6$ is an 0-protecting group (such as benzyl) with a compound of the formula X

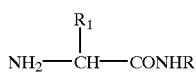 (X)

under conditions well known in the art for peptide synthesis.

The condensation with a free carboxylic add of formula IX is carried out advantageously in the presence of a condensing agent such as dicyclohexylcarbodiimide or N-(3-dimethylaminopropyl)-N'-ethylcarbodiimide in the presence of 1-hydroxy-7-azabenzotriazole, 1-hydroxybenzotriazole or benzotriazol-1-yloxytris(dimethylamino)phosphonium hexafluorophosphate (BOP Reagent), and of triethylamine or N-methylmorpholine, in an inert polar solvent such as dimethylformamide or methylene chloride, preferably at room temperature.

Reactive functional derivatives of carboxylic acids of formula IX are preferably acid halides (e.g. the acid chloride) and mixed anhydrides, such as the pivaloyl or isobutyloxycarbonyl anhydride, or activated esters such as the benzotriazole, 7-azabenzotriazole or hexafluorophenyl ester.

The condensation with a reactive functional derivative of an add of formula IX in the form of an acid halide, advantageously an acid chloride, or mixed anhydride, is carried out in an inert solvent such as toluene or methylene chloride, advantageously in the presence of a base, e.g. an inorganic base such as potassium carbonate or an organic base such as triethylamine, N-methylmorpholine or pyridine, preferably at room temperature.

As to the synthesis of the intermediates of formula IX, such can be prepared by condensation of a compound of formula XI

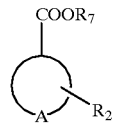 (XI)

wherein COOR$_7$ represents esterified carboxyl, e.g. lower alkoxycarbonyl, with e.g. a compound of the formula XII

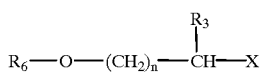 (XII)

wherein R$_6$ is an O-protecting group (such as benzyl) and X is reactive esterified hydroxyl, such as halo or alkylsulfonyloxy, in the presence of a strong anhydrous base, such as lithium diethylamide, in a solvent such as tetrahydrofuran.

The described condensation for the preparation of intermediates of formula IX (when R$_2$ is not hydrogen) which can lead to cis and trans isomers occurs in a stereoselective fashion. For example, the condensation of 4-R$_2$-substituted cyclohexanecarboxylic acid esters with e.g. benzyloxymethyl chloride leads predominantly to intermediates in which the R$_2$ and carboxyl groups are cis to each other. Such cis intermediates can then be converted to final products of formula IV (with stereochemistry as indicated) using an L-aminoacid amide in the subsequent condensation.

The starting materials of formula X, XI and XII are known in the art or can be prepared according to analogous methods known in the art.

Alternately, the compounds of formula I can be prepared by condensing a compound of the formula XIII

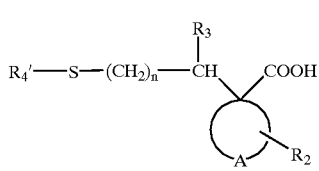 (XIII)

or a reactive functional derivative thereof wherein A, n, R$_2$ and R$_3$ have meaning as defined hereinabove and R$_4$' represents an S-protecting group, e.g. acyl, t-butyl or optionally substituted benzyl, with a compound of formula X

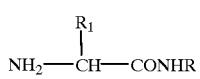 (X)

wherein R and R$_1$ have meaning as defined above.

This method is advantageously used for compounds wherein R$_3$ is other than hydrogen.

The intermediates of formula XIII can in turn be prepared by treating a compound of the formula

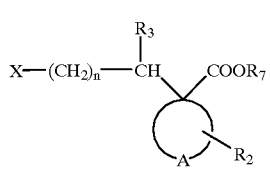 (XIV)

wherein A, X, n, R$_2$ and R$_3$ have meaning as defined hereinabove and COOR$_7$ represents esterified carboxyl, e.g. lower alkoxycarbonyl with a compound of formula VI

R$_4$'—SH (VI)

or a metal salt thereof wherein R$_4$' has meaning as defined herein above.

The alcohol precursors to the starting materials of formula XIV can be obtained by essentially using methodology described above for the synthesis of intermediates of formula IX, and deprotecting t he corresponding O—R$_6$ protected intermediates.

The alcohol precursors to the intermediates of formula XIII wherein n is zero can be advantageously prepared by condensing a compound of formula XI

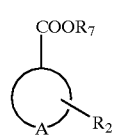 (XI)

wherein COOR$_7$ is esterified carboxyl with an aldehyde of the formula XV

R$_3$—CHO (XV)

under anhydrous basic conditions, e.g. in the presence of lithium diethylamide, to yield a compound of formula XVI

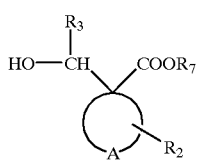

(XVI)

which can in turn be converted to the corresponding reactive intermediate of formula XIV wherein n is zero.

The above-mentioned reactions are carried out according to standard methods, in the presence or absence of diluent, preferably such as are inert to the reagents and are solvents thereof, of catalysts, condensing or said other agents respectively and/or inert atmospheres, at low temperatures, room temperature or elevated temperatures (preferably at or near the boiling point of the solvents used), and at atmospheric or super-atmospheric pressure. The preferred solvents, catalysts and reaction conditions are set forth in the appended illustrative examples.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure antipodes. Compounds of the invention and intermediates can also be converted into each other according to methods generally known per se.

The free mercaptans may be converted to the S-acyl derivatives by reaction with a reactive derivative of a carboxylic acid (corresponding to the acyl group $R_4$ in formula 1), such as an acid anhydride or acid chloride, preferably in the presence of cobalt chloride ($CoCl_2$) in an inert solvent such as acetonitrile or methylene chloride.

The free mercaptans, wherein $R_4$ represents hydrogen, may be oxidized to the corresponding disulfides, e.g. by air oxidation or with the use of mild oxidizing agents such as iodine in alcoholic solution. Conversely, disulfides may be reduced to the corresponding mercaptans, e.g. with reducing agents such as sodium borohydride, zinc and acetic acid or tributylphosphine. Carboxylic acid esters may be prepared from a carboxylic acid by condensation with e.g. the halide corresponding to $R_2$—OH, in the presence of a base, or with an excess of the alcohol in the presence of an acid catalyst, according to methods well-known in the art.

Carboxylic acid esters and S-acyl derivatives may be hydrolyzed, e.g. with aqueous alkali such as alkali metal carbonates or hydroxides.

The invention also relates to any novel starting materials and processes for their manufacture.

Depending on the choice of starting materials and methods, the new compounds may be in the form of one of the possible isomers or mixtures thereof, for example, as substantially pure geometric (cis or trans) isomers, optical isomers (antipodes), racemates, or mixtures thereof. The aforesaid possible isomers or mixtures thereof are within the purview of this invention.

Any resulting mixtures of isomers can be separated on the basis of the physico-chemical differences of the constituents, into the pure geometric or optical isomers, diastereoisomers, racemates, for example by chromatography and/or fractional crystallization.

Any resulting racemates of final products or intermediates can be resolved into optical antipodes by known methods, e.g. by separation of the diastereoisomeric salts thereof, obtained with an optically active acid or base, and liberating the optically active acidic or basic compound.

The carboxylic acid intermediates can thus be resolved into their optical antipodes e.g. by fractional crystallization of d- or l-(alpha-methylbenzylamine, cinchonidine, cinchonine, quinine, quinidine, ephedrine, dehydroabietylamine, brucine or strychnine)-salts. Racemic products can also be resolved by chiral chromatography, e.g. high pressure liquid chromatography using a chiral adsorbent.

Finally, compounds of the invention are either obtained in the free form, or as a salt thereof if salt forming groups are present.

Acidic compounds of the invention may be converted into salts with pharmaceutically acceptable bases, e.g. an aqueous alkali metal hydroxide, advantageously in the presence of an ethereal or alcoholic solvent, such as a lower alkanol. From the solutions of the latter, the salts may be precipitated with ethers, e.g. diethyl ether. Resulting salts may be converted into the free compounds by treatment with acids. These or other salts can also be used for purification of the compounds obtained.

Compounds of the invention having basic groups can be converted into acid addition salts, especially pharmaceutically acceptable salts. These are formed, for example, with inorganic acids, such as mineral acids, for example sulfuric acid, a phosphoric or hydrohalic acid, or with organic carboxylic acids, such as ($C_1$–$C_4$)-alkanecarboxylic acids which, for example, are unsubstituted or substituted by halogen, for example acetic acid, such as saturated or unsaturated dicarboxylic acids, for example oxalic, succinic, maleic or fumaric acid, such as hydroxycarboxylic acids, for example glycolic, lactic, malic, tartaric or citric acid, such as amino acids, for example aspartic or glutamic acid, or with organic sulfonic acids, such as ($C_1$–$C_4$)-alkylsulfonic acids (for example methanesulfonic acid) or arylsulfonic acids which are unsubstituted or substituted (for example by halogen). Preferred are salts formed with hydrochloric acid, methanesulfonic add and maleic acid.

In view of the close relationship between the free compounds and the compounds in the form of their salts, whenever a compound is referred to in this context, a corresponding salt is also intended, provided such is possible or appropriate under the circumstances.

The compounds, including their salts, can also be obtained in the form of their hydrates, or include other solvents used for their crystallization.

The pharmaceutical compositions according to the invention are those suitable for enteral, such as oral or rectal, transdermal and parenteral administration to mammals, including man, to inhibit matrix-degrading metalloproteinases, and for the treatment of disorders responsive thereto, comprising an effective amount of a pharmacologically active compound of the invention, alone or in combination, with one or more pharmaceutically acceptable carriers.

The pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with a) diluents, e.g. lactose, dextrose, sucrose, mannitol, sorbitol, cellulose and/or glycine; b) lubricants, e.g. silica, talcum, stearic acid, its magnesium or calcium salt and/or polyethyleneglycol; for tablets also c) binders e.g. magnesium aluminum silicate, starch paste, gelatin, tragacanth, methylcellulose, sodium carboxymethylcellulose and or polyvinylpyrrolidone; if desired d) disintegrants, e.g. starches, agar, alginic acid or its sodium salt, or effervescent mixtures; and/or e) absorbants, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1 to 75%, preferably about 1 to 50%, of the active ingredient.

Suitable formulations for transdermal application include an effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable formulations for topical application, e.g. to the skin and eyes, are preferably aqueous solutions, ointments, creams or gels well-known in the art.

The pharmaceutical formulations contain an effective matrix-degrading metalloproteinase inhibiting amount of a compound of the invention as defined above, either alone or in combination with another therapeutic agent, e.g. an anti-inflammatory agent with cyclooxygenase inhibiting activity, or other antirheumatic agents such as methotrexate, each at an effective therapeutic dose as reported in the art. Such therapeutic agents are well-known in the art.

Examples of antiinflammatory agents with cyclooxygenase inhibiting activity are diclofenac, naproxen, ibuprofen, and the like.

In conjunction with another active ingredient, a compound of the invention may be administered either simultaneously, before or after the other active ingredient, either separately by the same or different route of administration or together in the same pharmaceutical formulation.

The dosage of active compound administered is dependent on the species of warm-blooded animal (mammal), the body weight, age and individual condition, and on the form of administration. A unit dosage for oral administration to a mammal of about 50 to 70 kg may contain between about 10 and 1000 mg, advantageously between about 25 and 500 mg of the active ingredient.

The present invention also relates to methods of using the compounds of the invention and their pharmaceutically acceptable salts, or pharmaceutical compositions thereof, in mammals for inhibiting the matrix-degrading metalloproteinases, e.g. stromelysin, gelatinase, collagenase and macrophage metalloelastase, for inhibiting tissue matrix degradation, and for the treatment of matrix-degrading metalloproteinase dependent conditions as described herein, e.g. inflammation, rheumatoid arthritis, osteoarthritis, also tumors (tumor growth, metastasis, progression or invasion), pulmonary disorders, and the like described herein. Tumors (carcinomas) include mammalian breast, lung, bladder, colon, prostate and ovarian cancer, and skin cancer, including melanoma and Kaposi's sarcoma.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mm Hg (=20–133 mbar). The structure of final products, intermediates and starting materials is confirmed by standard analytical methods, e.g. microanalysis and spectroscopic characteristics (e.g. MS, IR, NMR). Abbreviations used are those conventional in the art. The concentration for $[\alpha]_D$ determinations is expressed in mg/ml.

EXAMPLE 1

(a) To a solution of 2-[N-(1-methanesulfonyloxymethyl4-methoxycyclohexanecarbonyl)-amino]-3-phenylpropionic acid N-phenylamide (1.63 g, 2.68 mmol) in acetonitrile (50 mL) is added potassium thioacetate (0.61 g, 5.36 mmol) The mixture is heated to reflux for 15 hours and then cooled. The organic phase is washed with brine, decolorized, and the solvent is removed to yield an oil. The oil is purified by flash chromatography (SiO$_2$, hexane/ethyl acetate, 1% methanol) to give (S)-2-[N-(1-(acetylmercaptomethyl)-cis-4-methoxycyclohexanecarbonyl)amino]-3-phenylpropionic acid N-phenylamide as a solid. $^1$H NMR (CDCl$_3$) $\delta$ 7.75 (s, 1H), 7.32 (m, 9H), 7.10 (t, 1H), 6.45 (d, 1H), 4.75 (q, 1H), 3.30 (s, 3H), 3.16 (m, 3H), 3.08 (s, 2H), 2.22 (s, 3H), 2.12–1.80 (m, 4H), 1.30 (m, 4H).

The starting materials are prepared as follows:

To a stirred solution of N-BOC-L-phenylalanine (20 g, 75.4 mmol) in methylene chloride (200 mL) is added aniline (7.0 mL, 75.4 mmol), dicyclohexylcarbodiimide (15.5 g, 75.4 mmol), and 1-hydroxy-7-azabenzotriazole (10.3 g, 75.4 mmol). The mixture is stirred at room temperature overnight. The solid is filtered away and the filtrate is washed with 5% citric acid (50 mL), a saturated solution of sodium bicarbonate (50 mL), and brine (50 mL). The organic phase is dried over magnesium sulfate, filtered, and concentrated under reduced pressure to yield a light brown solid. The solid is recrystallized from ethyl acetate to afford N-BOC-L-phenylalanine-N-phenylamide as a white solid (11 g).

To a solution of N-BOC-L-phenylalanine-N-phenylamide (1.7 g, 5 mmol) in methylene chloride (75 mL) is bubbled dry HCl gas for 15 minutes. The solvent is then removed under reduced pressure to give a white foam, mp 215–216° C. $^1$H NMR (DMSO-d$_6$) $\delta$ 10.9 (s, 1H), 8.5 (bs, 3H), 7.4–7.1 (m, 10H), 4.3 (t, 1H ), 3.15 (m, 2H).

To a solution of diisopropylamine (7.27 g, 72 mmol) in tetrahydrofuran (100 mL) at −50° C. is added 2.5 M n-butyl lithium (28.8 mL, 72 mmol). The mixture is warmed to 0° C. and stirred for 10 minutes. The solution is cooled to −50° C. and 4-methoxycyclohexylcarboxylic acid methyl ester (10.33 g, 60 mmol) is added dropwise. The mixture is allowed to slowly warm to 0° C. and is stirred for 30 minutes. The mixture is again cooled to 0° C. and then benzyl chloromethyl ether (11.3 g, 72 mmol) is added dropwise. The mixture is allowed to warm to room temperature and is stirred overnight. The solvent is then removed in vacuo and hexane is added to the residue. The organic phase is washed with 1N HCl, a saturated solution of sodium bicarbonate, and brine. The organic phase is dried over magnesium sulfate, filtered and the solvent is removed in vacuo to give an oil. The oil is dissolved in ethanol (70 mL) and water (70 mL) and potassium hydroxide (6.84 g, 120 mmol) is added. The mixture is heated to reflux for 16 hours and then concentrated in vacuo. A 1N solution of sodium hydroxide is added and the aqueous phase is washed with ether and then acidified with concentrated HCl. The aqueous phase is extracted with ethyl acetate, dried over magnesium sulfate, filtered, and the solvent is removed to give a solid. The solid is washed with hexane and dried at 50° C. to afford cis-1-benzyloxymethyl-4-methoxycyclohexanecarboxylic acid as a white solid.

To a solution of cis-1-benzyloxymethyl-4-methoxycyclohexanecarboxylic acid (1.39 g, 5 mmol) in methylene chloride (50 mL) is added L-phenylalanine-N-phenylamide (1.38 g, 5 mmol), triethylamine (0.51 g, 5 mmol), 1-hydroxy-7-azabenzotriazole (0.82 g, 6 mmol) and 1-(3-dimethylaminopropyl)-3-ethylcarbodiimide(1.15 g, 6 mmol). The mixture is stirred at room temperature overnight and then the organic phase is washed with a saturated solution of sodium bicarbonate, 5% citric acid, and brine. The solution is dried over magnesium sulfate, filtered and concentrated in vacuo to give (S)-2-[N-(1-benzyloxymethyl-cis4-methoxy-cyclo-hexanecarbonyl)amino]-3-phenylpropionic acid N-phenylamide as an oil.

A solution of (S)-2-[N-(1-benzyloxymethyl-cis-4-methoxycyclohexanecarbonyl)amino]-3-phenylpropionic acid N-phenylamide (2.40 g, 4.8 mmol) in ethanol (75 mL) and concentrated HCl (0.5 mL) with 10% Pd/C (0.24 g) is hydrogenated on a Parr hydrogenation apparatus for 90 minutes at 60 psi. The catalyst is removed by filtration and concentrated in vacuo to give 2-[N-(1-hydroxymethyl-4-methoxycyclohexanecarbonyl)amino]-3-phenylpropionic acid N-phenylamide as an oil. $^1$H NMR (CDCl$_3$) δ 8.35 (s, 1H), 7.25 (m, 10H), 7.06 (t, 1H), 4.3 (t, 1H), 6.48 (d, 1H), 4.88 (q, 1H), 3.46 (dq, 2H), 3.29 (s, 3H), 3.16 (d, 2H), 3.02 (m, 1H), 2.08 (m, 2H), 1.87 (m, 2H), 1.22 (m, 4H).

To a solution of (S)-2-[N-(1-hydroxymethyl-cis-4-methoxycyclohexanecarbonyl)amino]-3-phenylpropionic acid N-phenylamide (1.1 g, 2.68 mmol) in methylene chloride (50 mL) is added triethylamine (1.78 mL, 13.4 mmol) and mesyl chloride (1.53 g, 13.4 mmol). The mixture is stirred at room temperature for 1 hour and then the organic phase is removed. The residue is dissolved in methylene chloride (100 mL) and washed with a saturated solution of sodium bicarbonate, 5% citric acid, brine, and then dried over magnesium sulfate. The solution is filtered and concentrated to give an oil which is purified by flash chromatography (SiO$_2$,:2.5: 0.5, hexane:ethyl acetate:methanol). (S)-2-[N-(1-Methanesulfonyloxymethyl-cis-4-methoxycyclohexanecarbonyl)amino]-3-phenylpropionic acid N-phenylamide is obtained as a clear oil.

Similarly prepared are:

(b) (S)-2-[N-(1-(acetylmercaptomethyl)-cis-4-ethoxycyclohexanecarbonyl)amino]-3-phenylpropionic acid N-phenylamide, mp 145–146° C.;

(c) (S)-2-[N-(1-(1-acetylmercapto-3-phenylpropyl)cyclohexanecarbonyl)amino]-3-phenylpropionic acid N-methylamide, mp 60–64° C.;

(d) (S)-2-[N-(1-(1-acetylmercapto-3-phenylpropyl)-cis-4-methoxycyclohexanecarbonyl)-amino]-3-cyclohexylpropionic acid N-methylamide, mp 160–161° C.;

(e) (S)-2-[N-(1(acetylmercaptomethyl)-cis-4-methoxycyclohexanecarbonyl)amino]-4-methylpentanoic acid N-methylamide, mp 138–139° C.

(f) (S)-2-[N-(1-(acetylmercaptomethyl)-cis-4-ethoxycyclohexanecarbonyl)amino]-3-(2-thienyl) propionic acid N-phenylamide, mp 148–150° C.

(g) (S)-2-[N-(1-(acetylmercaptomethyl)-cis-4-ethoxycyclohexanecarbonyl)amino]-3-phenylpropionic acid N-(2-methoxyphenyl)amide, mp 128–129° C.

(h) (S)-2-[N-(1-(acetylmercaptomethyl)-cis-4-ethoxycyclohexanecarbonyl)amino]-3-phenylpropionic acid N-(4-fluorophenyl)amide, mp 142–143° C.

(i) (S)-2-[N-(1-(acetylmercaptomethyl)-cis-4-ethoxycyclohexanecarbonyl)amino]-3-phenylpropionic acid N-(3,5-dimethoxyphenyl)amide, mp 148–149° C.

(j) (S)-2-[N-(1-(acetylmercaptomethyl)-cis-4-ethoxycyclohexanecarbonyl)amino]-3-(4-t-butoxyphenyl)propionic acid N-phenylamide, mp 130–132° C.

(k) (S)-2-[N-(1-(acetylmercaptomethyl)-cis-4-ethoxycyclohexanecarbonyl)amino]-3-(4-hydroxyphenyl)propionic acid N-phenylamide, mp 77–78° C.

(l) (S)-2-[N-(1-(acetylmercaptomethyl)-cis-4-ethoxycyclohexanecarbonyl)amino]-3-phenylpropionic acid N-(3-methoxyphenyl)amide, mp 132–133° C.

(m) (S)-2-[N-(1-(acetylmercaptomethyl)-cis-4-ethoxycyclohexanecarbonyl)amino]-3-(4-methoxyphenyl)propionic acid N-phenylamide, mp 139–141 ° C.

(n) (S)-2-[N-(1-(acetylmercaptomethyl)-cis-4-ethoxycyclohexanecarbonyl)amino]-3-phenylpropionic add N-(4-ethoxyphenyl)amide, mp 155–156° C.

(o) (S)-2-[N-(1-(acetylmercaptomethyl)-cis-4-ethoxycyclohexanecarbonyl)amino]-3-phenylpropionic acid N-(4-trifluoromethoxyphenyl)amide, mp 138–139° C.

(p) (S)-2-[N-(1-(acetylmercaptomethyl)-cis-4-ethoxycyclohexanecarbonyl)amino]-3-(3-pyridyl) propionic acid N-phenylamide, mp 135–137° C.

(q) (S)-2-[N-(1-(acetylmercaptomethyl)-cis-4-ethoxycyclohexanecarbonyl)amino]-3-phenylpropionic add N-(4-chlorophenyl)amide, mp 170–171° C.

(r) (S)-2-[N-(1-(acetylmercaptomethyl)-cis-4-ethoxycyclohexanecarbonyl)amino]-3-(4-fluorophenyl) propionic acid N-phenylamide, mp 127–129° C.

(s) (S)-2-[N-(1-(acetylmercaptomethyl)-cis-4-methoxycyclohexanecarbonyl)amino]-3-phenylpropionic acid N-(4-fluorophenyl)amide, mp 160–161 ° C.

(t) (S)-2-[N-(1-(acetylmercaptomethyl)-cis-4-ethoxycyclohexanecarbonyl)amino]-3-phenylpropionic acid N-(4-methylthiophenyl)amide, mp 146–147° C.

(u) (S)-2-[N-(1-(acetylmercaptomethyl)-cis4-ethoxycyclohexanecarbonyl)amino]-3-phenylpropionic acid N-(4-N,N-dimethylaminophenyl)amide, mp 127° C.

(v) (S)-2-[N-(1-(acetylmercaptomethyl)-cis-4-methoxycyclohexanecarbonyl)amino]-3-phenylpropionic acid N-(3,5-dimethoxyphenyl)amide, mp 162–163° C.

(w) (S)-2-[N-(1-(acetylmercaptomethyl)-cis-4-methoxycyclohexanecarbonyl)amino]-3-phenylpropionic acid N-benzylamide, mp 149–150° C.

(x) (S)-2-[N-(1-(acetylmercaptomethyl)-cis-4-methoxycyclohexanecarbonyl)amino]-3-phenylpropionic acid N-(3-pyridyl)amide, mp 143–144° C.

(y) (S)-2-[N-(1-(methoxyacetylmercaptomethyl)-cis-4-methoxycyclohexanecarbonyl)amino]-3-phenylpropionic acid N-(4-methoxyphenyl)amide, mp 138–139° C.

(z) (S)-2-[N-(1-(benzoylmercaptomethyl)-cis-4-ethoxycyclohexanecarbonyl)amino]-3-phenylpropionic acid N-(4-methoxyphenyl)amide, mp 165–166° C.

(aa) (S)-2-[N-(1-(morpholinoacetylmercaptomethyl)-cis-4-ethoxycyclohexanecarbonyl)amino]-3-phenylpropionic acid N-(4-methoxyphenyl)amide, mp 172–173° C.

(bb) (S)-2-[N-(1-((2-pyridinylcarbonyl)mercaptomethyl)-cis-4-ethoxycyclohexanecarbonyl)amino]-3-phenylpropionic acid N-(4-methoxyphenyl)amide, mp 87–88° C.

(cc) (S)-2-[N-(1-(butanoylmercaptomethyl)-cis-4-ethoxycyclohexanecarbonyl)amino]-3-phenylpropionic acid N-(4-methoxyphenyl)amide, mp 144–145° C.

(dd) (S)-2-[N-(1-((2-thienylcarbonyl)mercaptomethyl)-cis-4-ethoxycyclohexanecarbonyl)amino]-3-phenylpropionic acid N-(4-methoxyphenyl)amide, foam.

(ee) (S)-2-[N-(1-(benzoylmercaptomethyl)-cis-4-ethoxycyclohexanecarbonyl)amino]-3-phenylpropionic acid N-(3-pyridyl)amide, mp 75–80° C.

EXAMPLE 2

(a) To a stirred degassed solution of (S)-2-[N-(1-acetylmercaptomethyl-cis-4-methoxy-cyclohexanecarbonyl)amino]-3-phenylpropionic acid N-phenylamide (0.60 g, 1.28 mmol) in methanol (30 mL) under nitrogen at room temperature is added degassed 1N NaOH (2.50 mL, 2.56 mmol). The solution is stirred for 1 hour and then acidified to pH 1 with 1N HCl. The methanol is removed in vacuo to yield a suspension of a yellow solid in water. The solid is collected by filtration, washed with water and dried in vacuo at 50° C. for 16 hours to give (S)-2-N-(1-mercaptomethyl-cis-4-methoxycyclohexanecarbonyl)amino]-3-phenylpropionic acid N-phenylamide, mp 171–172° C. $^1$H NMR (CDCl$_3$) δ 7.94 (s, 1H), 7.30 (m, 9H), 7.09 (t,1H), 6.43 (d, 1H), 4.95 (q, 1H), 3.30 (s, 3H), 3.23 (dd, 2H), 3.16 (m, 2H), 2.67 (m, 2H), 2.13 (m, 2H), 1.82 (m, 2H), 1.33 (m, 4H). Anal cald. C, 67.58; H, 7.09; N, 6.57, found C, 67.39; H, 7.08; N, 6.48.

Similarly prepared are:

(b) (S)-2-[N-(1-mercaptomethyl-cis-4-ethoxycyclohexanecarbonyl)amino]-3-phenylpropionic acid N-isopropylamide, mp 159–160° C.;

(c) (S)-2-[N-(1-mercaptomethyl-cis-4-ethoxycyclohexanecarbonyl)amino]-3-phenylpropionic acid N-benzylamide, mp 91–92° C.

(d) (S)-2-[N-(1-(1-mercapto-3-phenylpropyl)-cyclohexanecarbonyl)amino]-3-phenylpropionic acid N-methylamide, mp 61–65° C;

(e) (S)-2-[N-(1-mercaptomethyl-cis-4-ethoxycyclohexanecarbonyl)amino]-3-phenylpropionic acid N-phenylamide, mp 163–164° C.;

(f) (S)-2-[N-(1-mercaptomethyl-4-trifluoromethylcyclohexanecarbonyl)amino]-3-phenyl-propionic acid N-methylamide, mp 157.5–158.5° C.;

(g) (S)-2-[N-(1-mercaptomethyl-cis-4-ethoxycyclohexanecarbonyl)amino]-3-phenylpropionic acid N-methylamide, mp 111–112° C.;

(h) (S)-2-[N-(1-mercaptomethyl-cis-4-methoxycyclohexanecarbonyl)amino]-3-cyclohexyl-propionic acid N-methylamide, mp 161–162° C.;

(i) (S)-2-[N-(1-mercaptomethyl-cis-4-methoxycyclohexanecarbonyl)amino]-phenylacetic acid N-methylamide, mp 84–86° C.;

(j) (S)-2-[N-(1-(mercaptomethyl)-cycloheptanecarbonyl)amino]-3-phenylpropionic add N-methylamide, mp 128–129° C.;

(k) (S)-2-[N-(1-mercaptomethyl-cis-4-propylcyclohexanecarbonyl)amino]-3-phenylpropionic acid N-methylamide, mp 136–137° C.;

(l) (S)-2-[N-(1-mercaptomethyl-cis-4-methoxycyclohexanecarbonyl)-amino]4-methyl-pentanoic acid N-methylamide, mp 106–108° C.;

(m) 2-[N-(1-mercaptomethyl-cis-4-methoxycyclohexanecarbonyl)amino]-3(4-biphenyl) propionic acid N-methylamide, mp 135–136° C.;

(n) (S)-2-[N-(1-mercaptomethyl-cis-4-t-butylcyclohexanecarbonyl)amino]-3-phenylpropionic acid N-methylamide, 122–124° C.;

(o) (S)-2-[N-(1-mercaptomethyl-cis-4-propoxycyclohexanecarbonyl)amino]-3-phenylpropionic acid N-methylamide, mp 50–52° C.;

(p) (S)-2-[N-(1-mercaptomethyl-cis-4-(2-phenylethoxy)cyclohexanecarbonyl)amino]-3-phenylpropionic acid N-methylamide, mp 49–52° C.;

(q) 2-[N-(1-mercaptomethyl-cis-4-methoxycyclohexanecarbonyl)amino]-3-(4-methoxyphenyl)propionic acid N-methylamide, mp 118–119° C.;

(r) (S)-2-[N-(1-mercaptomethyl-3-methoxycyclohexanecarbonyl)amino]-3-phenylpropionic acid N-methylamide, oil.

(s) (S)-2-[N-(1-mercaptomethyl-4-methoxycyclohexanecarbonyl)-amino]-3-phenylpropionic acid N-methylamide, mp 125–126° C.;

(t) (S)-2-[N-(1-(mercaptomethyl-cyclohexanecarbonyl)-amino]4-phenylbutanoic acid N-methylamide, mp 165° C.;

(u) (S)-2-[N-(1-mercaptomethyl-cyclohexanecarbonyl)-amino]-3-phenylpropionic acid N-methylamide, mp 85–88° C.;

(v) (S)-2-[N-(1-mercaptomethyl-cis-4-methoxycyclohexanecarbonyl)amino]-4-methyl-pentanoic acid N-(diphenylmethyl)amide, mp 142–144° C.;

(w) (S)-2-[N-(1-(3-mercaptopropyl)-cis-4-methoxycyclohexanecarbonyl)amino]-3-phenyl-propionic acid N-methylamide, mp 101–102° C.

(x) (S)-2-[N-(1-mercaptomethyl-cis-4-ethoxycyclohexanecarbonyl)amino]-3-phenylpropionic acid N-(4-chlorophenyl)amide, mp 175–176° C.

(y) (S)-2-[N-(4-mercaptomethyl-cis-4-ethoxycyclohexanecarbonyl)amino]-3-phenylpropionic acid N-(2-fluorophenyl)amide, mp 99–100° C.

(z) (S)-2-[N-(1-mercaptomethyl-cis-4-ethoxycyclohexanecarbonyl)amino]-3-phenylpropionic acid N-(2-methoxyphenyl)amide, mp 97–98° C.

(aa) (S)-2-[N-(1-mercaptomethyl-cis-4-ethoxycyclohexanecarbonyl)amino]-3-phenylpropionic acid N-(4-fluorophenyl)amide, mp 152–153° C.

(bb) (S)-2-[N-(1-mercaptomethyl-cis-4-ethoxycyclohexanecarbonyl)amino]-3-phenylpropionic acid N-(3,5-dimethoxyphenyl)amide, mp 166–167° C.

(cc) (S)-2-[N-(1-mercaptomethyl-cis-4-ethoxycyclohexanecarbonyl)amino]-3-(4-hydroxyphenyl)propionic acid N-phenylamide, mp 100–101° C.

(dd) (S)-2-[N-(1-mercaptomethyl-cis-4-ethoxycyclohexanecarbonyl)amino]-3-phenylpropionic acid N-(3-methoxyphenyl)amide, mp 114–115° C.

(ee) (S)-2-[N-(1-mercaptomethyl-cis-4-ethoxycyclohexanecarbonyl)amino]-3-phenylpropionic acid N-(4-ethoxyphenyl)amide, mp 155–156 0C.

(ff) (S)-2-[N-(1-mercaptomethyl-cis-4-ethoxycyclohexanecarbonyl)amino]-3-phenylpropionic acid N-(4-trifluoromethoxyphenyl)amide, mp 179–180° C.

(gg) (S)-2-[N-(1-mercaptomethyl-cis-4-ethoxycyclohexanecarbonyl)amino]-3-phenylpropionic acid N-(2-pyridyl)amide, mp 124–125° C.

(hh) (S)-2-[N-(1-mercaptomethyl-cis-4-ethoxycyclohexanecarbonyl)amino]-3-phenylpropionic acid N-(4-methylthiophenyl)amide, mp 189–190° C.

(ii) (S)-2-[N-(1-mercaptomethyl-cis-4-methoxycyclohexanecarbonyl)amino]-3-phenylpropionic acid N-(4-fluorophenyl)amide, mp 173–174° C.

(jj) (S)-2-[N-(1-mercaptomethyl-cis-4-ethoxycyclohexanecarbonyl)amino]-3-phenylpropionic acid N-(4-N,N-dimethylaminophenyl)amide, mp 162–163° C.

(kk) (S)-2-[N-(1-mercaptomethyl-cis-4-methoxycyclohexanecarbonyl)amino]-3-phenylpropionic acid N-(3,5-dimethoxyphenyl)amide, mp 189–190° C.

(ll) (S)-2-[N-(1-mercaptomethyl-cis-4-ethoxycyclohexanecarbonyl)amino]-3-phenylpropionic acid N-(4-carboxyphenyl)amide, mp 231–232° C.

(mm) (S)-2-[N-(1-mercaptomethyl-cis-4-ethoxycyclohexanecarbonyl)amino]-3-phenylpropionic acid N-(cyclopentyl)amide, mp 189–190° C.

(nn) (S)-2-[N-(1-mercaptomethyl-cis-4-ethoxycyclohexanecarbonyl)amino]-3-phenylpropionic acid N-(cyclohexyl)amide, mp 159–160° C.

(oo) (S)-2-[N-(1-mercaptomethyl-cis-4-ethoxycyclohexanecarbonyl)amino]-3-phenylpropionic acid N-(2-thienylmethyl)amide, mp 137–138° C.

(pp) (S)-2-[N-(1-mercaptomethyl-cis-4-ethoxycyclohexanecarbonyl)amino]-3-(3-pyridyl)-propionic acid N-(phenyl)amide, mp 77–78° C.

(qq) (S)-2-[N-(1-mercaptomethyl-cis-4-ethoxycyclohexanecarbonyl)amino]-3-(4-chlorophenyl)propionic acid N-(phenyl)amide, mp 180–181° C.

(rr) (S)-2-[N-(1-mercaptomethyl-cis-4-ethoxycyclohexanecarbonyl)amino]-3(4-methoxyphenyl)propionic acid N-(phenyl)amide, mp 170–171° C.

(ss) (S)-2-[N-(1-mercaptomethyl-cis-4-ethoxycyclohexanecarbonyl)amino]-3-phenylpropionic acid N-(4-methoxyphenyl)amide, mp 151–152° C.

(tt) (S)-2-[N-(1-mercaptomethyl-cis-4-ethoxycyclohexanecarbonyl)amino]-3-(2-thienyl) propionic acid N-(phenyl)amide, mp 129–130° C.

(uu) (S)-2-[N-(1-mercaptomethyl-cis-4-ethoxycyclohexanecarbonyl)amino]-3-phenylpropionic acid N-(3-pyridyl)amide, mp 133–137° C.

(vv) (S)-2-[N-(1-mercaptomethyl-cis-4-ethoxycyclohexanecarbonyl)amino]-3-(4-fluorophenyl) propionic acid N-(phenyl)amide, mp 177–178° C.

EXAMPLE 3

Similarly prepared to the compounds in the previous examples are:

(a) (S)-2-[N-(4-mercaptomethyl-1-acetylpiperidyl-4-carbonyl)-amino]-3-phenylpropionic acid N-methylamide, mp 76–78° C.;

(b) (S)-2-[N-(4-mercaptomethyl-1-methylsulfonylpiperidyl-4-carbonyl)amino]-3-phenyl-propionic acid N-methylamide, mp 73–74° C;

(c) (S)-2-[N-(4-mercaptomethyl-1-benzylpiperidyl-4-carbonyl)amino]-3-phenylpropionic acid N-methylamide, mp 45°.

(d) (S)-2-[N-[1-(1-mercapto-2-methoxy)ethyl]-cis-4-methoxycyclohexanecarbonyl)amino]-3-phenylpropionic acid N-phenylamide.

(e) (S)-2-[N-(1-mercaptomethyl-cis-4-methoxycyclohexanecarbonyl)-amino]-3-phenyl-propionic acid N-(morpholinomethyl)-amide.

(f) (S)-2-[N-(1-mercaptomethyl-cis-4-(propionylamino)-cyclohexanecarbonyl)amino]-3-phenylpropionic acid N-phenylamide.

EXAMPLE 4

Preparation of 3000 capsules each containing 25 mg of the active ingredient, for example 2-[N-(1-(acetylmercaptomethyl)4-methoxycyclohexanecarbonyl) amino]-3-phenylpropionic acid N-phenylamide

| Active ingredient | 75.00 g |
| Lactose | 750.00 g |
| Microcrystalline cellulose | 300.00 g |
| Polyvinylpyrrolidone | 30.00 g |
| Purified water | q.s. |
| Magnesium stearate | 9.0 |

The active ingredient is passed through a No. 30 hand screen.

The active ingredient, lactose, cellulose and polyvinylpyrrolidone are blended for 15 minute in a mixer. The blend is granulated with sufficient water (about 500 mL), dried in an oven at 35° C. overnight, and passed through a No. 20 screen.

Magnesium stearate is passed through a No. 20 screen, added to the granulation mixture, and the mixture is blended for 5 minutes in a mixer. The blend is encapsulated in No. 0 hard gelatin capsules each containing an amount of the blend equivalent of 10 mg of the active ingredient.

I claim:

1. A compound of the formula

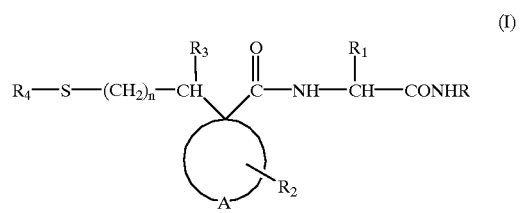

(I)

wherein

R represents hydrogen, lower alkyl, cycloalkyl, bicycloalkyl, adamantyl, aryl, biaryl, or mono- or di-(cycloalkyl, aryl or biaryl)-lower alkyl, di-(lower alkyl or aryl-lower alkyl)amino-lower alkyl, or (piperidino, morpholino, pyrrolidino)-lower alkyl;

$R_1$ represents hydrogen, lower alkyl, cycloalkyl, aryl, biaryl, or (cycloalkyl, aryl or biaryl)-lower alkyl;

$R_2$ represents hydrogen, lower alkyl, lower alkoxy, aryl-lower alkyl, aryl-lower alkoxy, amino, mono- or di-(lower alkyl or aryl-lower alkyl)-amino, acylamino, or (lower alkyl or aryl-lower alkyl)-(thio, sulfinyl or sulfonyl);

$R_3$ represents hydrogen, lower alkyl, cycloalkyl, aryl-lower alkyl, cycloalkyl-lower alkyl, or $C_2$–$C_7$alkyl interrupted by S, SO, $SO_2$, O or N—$R_5$;

$R_4$ represents hydrogen or acyl;

$R_5$ represents hydrogen, lower alkyl, aryl-lower alkyl, acyl, or (lower alkyl, aryl or aryl-lower alkyl)-sulfonyl;

A together with the carbon to which it is attached forms a ring and represents a bivalent radical of the formula $(CH_2)_P$;

n represents zero or an integer from 1 to 4;

p represents an integer from 2 to 6;

provided that R may not represent hydrogen or lower alkyl if $R_2$ represents hydrogen or lower alkyl; and provided that $R_2$ may not represent hydrogen or lower alkyl if R represents hydrogen or lower alkyl;

or a pharmaceutically acceptable salt thereof; or a disulfide corresponding to said compound of formula I wherein $R_4$ is hydrogen.

2. A compound according to claim 1 of the formula

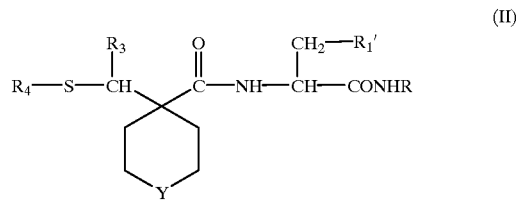

(II)

wherein

R, $R_2$, $R_3$ and $R_4$ and $R_5$ have meaning as defined above, $R_1'$ represents cycloalkyl, aryl or biaryl; and Y represents $CHR_2$.

3. A compound according to claim 1 of the formula III

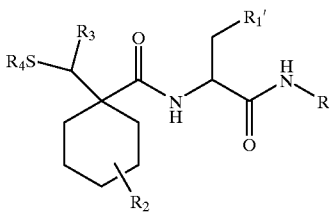

(III)

wherein R is carbocyclic or heterocyclic aryl, carbocyclic or heterocyclic aryl-lower alkyl, cycloalkyl or lower alkyl; $R_1'$ is carbocyclic or heterocyclic aryl, or biaryl; $R_2$ is lower alkoxy; $R_3$ is hydrogen, lower alkyl or carbocyclic aryl-lower alkyl; and $R_4$ is hydrogen, lower alkanoyl, aryl-lower alkanoyl or aroyl.

4. A compound according to claim 2 wherein the configuration of the asymmetric carbon atom of the terminal amino acid amide moiety corresponds to that of an L-amino acid precursor and is assigned the (S)-configuration.

5. A compound according to claim 3 wherein $R_2$ is at the 4-position of the cyclohexane ring.

6. A compound according to claim 3 of the formula

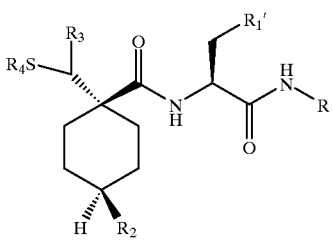

(IV)

wherein $R_2$ and the amide chain are cis to each other, and R, $R_1'$, $R_2$, $R_3$ and $R_4$ have meaning as defined in said claim; and wherein the configuration of the asymmetric carbon atom of the terminal amino acid amide is assigned the (S)-configuration.

7. A compound according to claim 6 wherein R is monocyclic carbocyclic or heterocyclic aryl; $R_1'$ is monocyclic carbocyclic aryl; $R_2$ is lower alkoxy; $R_3$ is hydrogen; and $R_4$ is hydrogen or lower alkanoyl.

8. A compound according to claim 3 which is 2-[N-(1-mercaptomethyl-4-ethoxycyclohexanecarbonyl)amino]-3-phenylpropionic acid N-methylamide.

9. A compound according to claim 3 which is (S)-2-[N-(1-mercaptomethyl-cis-4-methoxycyclohexanecarbonyl)amino]-3-phenylpropionic acid N-phenylamide.

10. A compound according to claim 3 which is (S)-2-[N-(1-mercaptomethyl-cis-4-ethoxycyclohexanecarbonyl)amino]-3-phenylpropionic acid N-methylamide.

11. A pharmaceutical composition comprising an effective matrix-degrading metalloproteinase inhibiting amount of a compound of claim 1 in combination with one or more pharmaceutically acceptable carriers.

12. A pharmaceutical composition comprising an effective matrix-degrading metalloproteinase inhibiting amount of a compound of claim 1 in combination with one or more pharmaceutically acceptable carriers.

13. A pharmaceutical composition comprising an effective matrix degrading metallaproteinase inhibiting amount of a compound of claim 3 in combination with one or more pharmaceutically acceptable carriers.

14. A method of inhibiting matrix-degrading metalloproteinases in mammals which comprises administering to a mammal in need thereof an effective matrix-degrading metalloproteinase inhibiting amount of a compound of claim 1.

15. A method of inhibiting matrix-degrading metalloproteinases in mammals which comprises administering to a mammal in need thereof an effective matrix-degrading metalloproteinase inhibiting amount of a compound of claim 3.

16. A method according to claim 15 wherein the metalloproteinase is collagenase.

17. A method of inhibiting matrix-degrading metalloproteinases in mammals which comprises administering to a mammal in need thereof an effective matrix-degrading metalloproteinase inhibiting amount of a compound of the formula

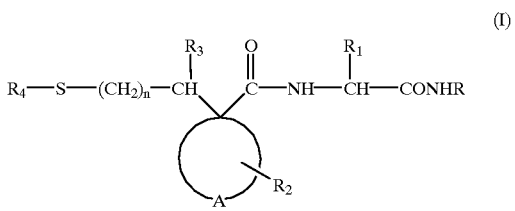

(I)

wherein

R represents hydrogen, lower alkyl, cycloalkyl, bicycloalkyl, adamantyl, aryl, biaryl, or mono- or di-(cycloalkyl, aryl or biaryl)-lower alkyl, di-(lower alkyl or aryl-lower alkyl)amino-lower alkyl, or (piperidino, morpholino, pyrrolidino)-lower alkyl;

$R_1$ represents hydrogen, lower alkyl, cycloalkyl, aryl, biaryl, or (cycloalkyl, aryl or biaryl)-lower alkyl;

$R_2$ represents hydrogen, lower alkyl, lower alkoxy, aryl-lower alkyl, aryl-lower alkoxy, amino, mono- or di-(lower alkyl or aryl-lower alkyl)-amino, acylamino, or (lower alkyl or aryl-lower alkyl)-(thio, sulfinyl or sulfonyl);

$R_3$ represents hydrogen, lower alkyl, cycloalkyl, aryl-lower alkyl, cycloalkyl-lower alkyl, or $C_2$–$C_7$-alkyl interrupted by S, SO, $SO_2$, O or N—$R_5$;

$R_4$ represents hydrogen or acyl;

$R_5$ represents hydrogen, lower alkyl, aryl-lower alkyl, acyl, or (lower alkyl, aryl or aryl-lower alkyl)-sulfonyl;

A together with the carbon to which it is attached forms a ring and represents a bivalent radical of the formula $(CH_2)_P$;

n represents zero or an integer from 1 to 4;

p represents an integer from 2 to 6;

or a pharmaceutically acceptable salt thereof; or a disulfide corresponding to said compound of formula I wherein $R_4$ is hydrogen.

18. A method according to claim 17 wherein the metalloproteinase is collagenase.

19. A method according to claim 17 which comprises the administration of a compound of the formula

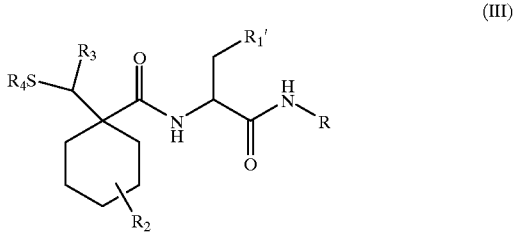

(III)

wherein R is carbocyclic or heterocyclic aryl, carbocyclic or heterocyclic aryl-lower alkyl, cycloalkyl or lower alkyl; $R_1'$ is carbocyclic or heterocyclic aryl, or biaryl; $R_2$ is hydrogen, lower alkyl or lower alkoxy; $R_3$ is hydrogen, lower alkyl or carbocyclic aryl-lower alkyl; and $R_4$ is hydrogen, lower alkanoyl, aryl-lower alkanoyl or aroyl.

* * * * *

UNITED STATES PATENT AND TRADEMARK OFFICE
CERTIFICATE OF CORRECTION

PATENT NO. : 6,034,136
DATED : March 7, 2000
INVENTOR(S) : Cynthia A. Fink

It is certified that error appears in the above-identified patent and that said Letters Patent is hereby corrected as shown below:

Cancel claim 12, column 25, lines 59-62.

Signed and Sealed this

Ninth Day of October, 2001

Attest:

NICHOLAS P. GODICI
Attesting Officer   Acting Director of the United States Patent and Trademark Office